United States Patent
Li et al.

(10) Patent No.: US 9,603,197 B2
(45) Date of Patent: Mar. 21, 2017

(54) SMART THERMAL TEXTILE FOR ACUPUNCTURE THERAPY

(75) Inventors: Li Li, Kowloon (CN); Raymond Wai-man Au, Kowloon (CN); Thomas K. S. Wong, Kowloon (CN); Yi Li, Kowloon (CN); Joanne W. Y. Chung, Kowloon (CN); Sai Ho Wan, Kowloon (CN)

(73) Assignee: The Hong Kong Polytechnic University, Kowloon (HK)

(*) Notice: Subject to any disclaimer, the term of this patent is extended or adjusted under 35 U.S.C. 154(b) by 1225 days.

(21) Appl. No.: 12/216,476

(22) Filed: Jul. 7, 2008

(65) Prior Publication Data

US 2010/0004720 A1    Jan. 7, 2010

(51) Int. Cl.
| | | |
|---|---|---|
| A61F 7/00 | (2006.01) |
| H05B 3/34 | (2006.01) |
| A41D 13/005 | (2006.01) |
| A61N 1/04 | (2006.01) |
| D04B 1/16 | (2006.01) |
| A41D 1/00 | (2006.01) |
| A61F 7/02 | (2006.01) |

(52) U.S. Cl.
CPC ......... *H05B 3/342* (2013.01); *A41D 13/0051* (2013.01); *A61F 7/007* (2013.01); *A61N 1/0408* (2013.01); *A61N 1/0484* (2013.01); *D04B 1/16* (2013.01); *A41D 1/002* (2013.01); *A61F 2007/0078* (2013.01); *A61F 2007/0234* (2013.01); *H05B 2203/005* (2013.01); *H05B 2203/007* (2013.01); *H05B 2203/036* (2013.01)

(58) Field of Classification Search
CPC ...... A61F 2007/0233; A61F 2007/0225; A61F 2007/0226; A61F 2007/023; A61F 2007/0078; A61F 2007/0234; A61F 7/007; H05B 3/342; H05B 3/345; H05B 3/347; H05B 2203/005; H05B 2203/007; H05B 2203/036; A61N 1/0484; A61N 1/0408; A41D 13/0051; A41D 1/002; D04B 1/16
USPC .......... 607/2, 146, 152, 112, 148, 149, 104, 607/108–111
See application file for complete search history.

(56) References Cited

U.S. PATENT DOCUMENTS

| | | | |
|---|---|---|---|
| 6,548,789 B1 * | 4/2003 | Rock et al. .................. 219/545 |
| 6,694,185 B2 | 2/2004 | Orton | |
| 7,233,828 B2 | 6/2007 | Vlad | |
| 2004/0237170 A1 * | 12/2004 | Yamazaki ............ A41D 19/015 2/159 |
| 2005/0127057 A1 * | 6/2005 | Rock et al. .................. 219/211 |

FOREIGN PATENT DOCUMENTS

| | | |
|---|---|---|
| CN | 2238628 Y | 10/1996 |
| CN | 201018935 Y | 2/2008 |
| CN | 101268868 A | 9/2008 |
| CN | 201186980 Y | 1/2009 |

* cited by examiner

*Primary Examiner* — Jason Flick
(74) *Attorney, Agent, or Firm* — McDonnell Boehnen Hulbert & Berghoff LLP

(57) ABSTRACT

The present invention relates to a smart textile capable of providing acupuncture therapy to the wearer through strategically positioned electrodes throughout the textile, connected via silver coated fabric. Through the instant invention, heat therapy can be applied to specific points on the body, while being safe due to the absence of wires.

3 Claims, 1 Drawing Sheet

Front

Back

SMART THERMAL TEXTILE FOR ACUPUNCTURE THERAPY

BACKGROUND

In the treatment of many types of diseases, pains, and disorders of the body, it is often advantageous to keep the afflicted area warm, or more desirable still, at an elevated skin temperature. This is true of the treatment of arthritis, neuritis, muscular ailments, and certain mechanical bone disorders. This heat therapy typically takes the form of wrapping the area to be treated with a brace or bandage, or applying a pad to the region which by reason of a low thermal conductance limits the escape of body heat.

Bandages, braces and pads made of low thermal conductivity material do serve to reduce heat loss, but are generally relatively thick since the degree of thermal nonconductance is a function of thickness. This adds unnecessary cost, weight and bulk to the support brace.

It is an object of the present invention to provide an improved means for providing heat to a bodily area.

DESCRIPTION

The present invention relates to a smart textile capable of providing acupuncture therapy to the wearer through strategically positioned heating pads throughout the textile, connected via conductive textiles. Through the present invention, heat therapy can be applied to specific points on the body, while being safe due to the absence of wires.

These and other features, aspects, and advantages of the apparatus and methods of the present invention will become better understood from the following description, appended claims, and accompanying drawings where:

The following description of certain exemplary embodiment(s) is merely exemplary in nature and is in no way intended to limit the invention, its application, or uses. As used herein, the phrase "traditional Chinese medicine" refers to a branch of natural medicine that emphasizes and uses every part, process, thought, and emotion within an individual as the healthy functioning of the whole person.

Figure 1:
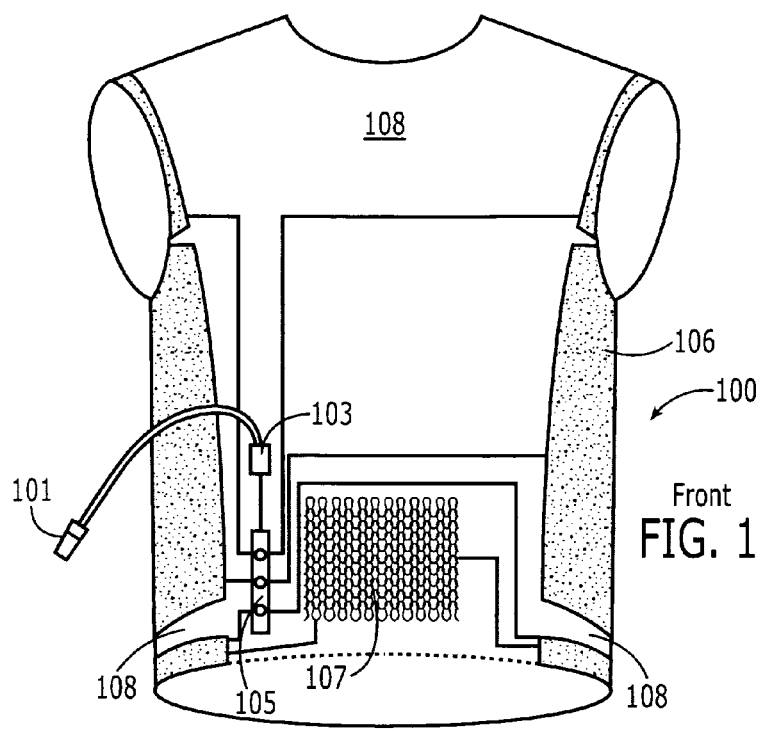
FIG. 1 shows an embodiment of the smart textile in the present invention.
Figure 2:
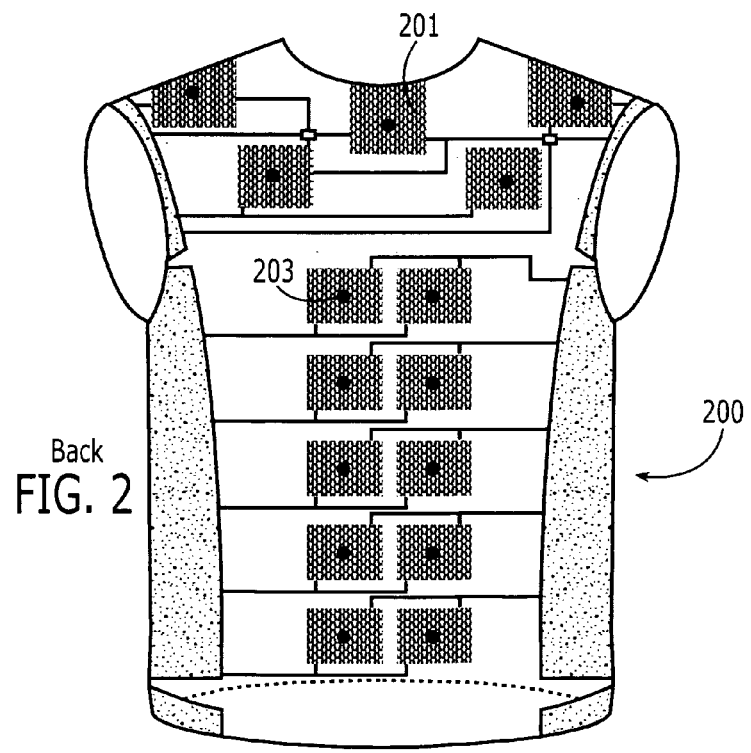
FIG. 2 shows an embodiment of another plane of the smart textile of the present invention.

Now, to FIGS. 1-2,

FIG. 1 is an embodiment of a smart textile 100 in accordance with the present invention. While this embodiment is in the form of a shirt, the textile can be underwear, sportswear, sweaters, knitwear, trousers, pants, briefs, brassieres, footwear, wrist/finger band support, ankle/foot band support, localized elbow and knee support bands, belts, bags, bed clothes, home products, or medical products.

On one plane of the textile 100, such as the front, an input 101 for accepting a power supply is present. Suitable inputs can include DC sources such as batteries, AC sources, Universal Serial Bus (USB) as an interfacing means with a computer system, renewable energy sources such as solar cells, and the like.

The electricity from the power supply can then be manipulated by a power modification means 103 such as a step-up transformer, step-down transformer, rectifier, filter, comparator, resistors, and the like, as needed in order to make the supplied power suitable for use by the smart textile.

Electricity to be conducted through the smart textile is controlled by an electronic controlling device 105. The electronic controlling device 105 is able to control which areas of the user's body, when wearing the textile, will receive treatment. The electronic controlling device 105 is also able to control the strength of the treatment by controlling the power flow through the smart textile 100.

From the electronic controlling device 105, electricity is forwarded to conductive textile 106 that forms part of the smart textile 100. The smart textile 100, in terms of materials, is made of normal yarn 108 and conductive textile 106. Normal yarn 108 can include spun yarn, thread, or yarns made from blends such as synthetic fibers, natural fibers. The normal yarn is not capable of conducting electricity. The conductive textile 106 occurs by knitting conductive yarns into sections of the knitted fabric of the smart textile 100. The manufacturing of the smart textile 100 can include knitted fabric by knitting conductive material, woven fabric by weaving conductive material, non-woven fabric with conductive fiber inside, fabric with sewn conductive thread or with cut conductive woven fabric, or embroidery by conductive thread. The smart textile is shown 107.

Electricity is conducted throughout the smart textile 100 via the conductive textile 106, and forwarded to heating pads strategically positioned throughout the textile 100 (to be discussed later).

FIG. 2 is an embodiment of another plane of a smart textile 200, such as the back of the textile. In this embodiment, the heating pads (i.e., 203 are strategically positioned to match Traditional Chinese Medicine acupuncture points along the shoulders, lower back, and abdominal areas. The strategic positioning can be particular acupuncture points or other particular areas according to Chinese Medicine for treating difficult diseases.

The heating pad is made of conductive textiles with small resistance. Specifically, the resistances of the heating pads 203 are higher than that of the conductive textiles 106 which are used for interconnections, so that most energy will be used by the heating pads 203 for heating.

Through the present invention, the smart textile is able to heat directly on the skin without the use of electrical wires. The smart textile can be dressed and used whenever and wherever, at the same time of doing other duties such as working, studying, playing, sleeping, cooking, or shopping. The textile can be used to apply both Western physical therapy methods and traditional Chinese medicinal therapy methods. The textile, owning to the lack of electrical wires, is capable of being washed and lightweight.

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. A smart textile for providing acupuncture therapy to a user, comprising,
   - a power supply configured to supply power to the smart textile;
   - conductive textiles which are capable of conducting electricity, the conductive textiles are configured to directly receive power from the power supply, the conductive textiles are made with a first conductive textile material having a first resistance, the conductive textiles are manufactured by weaving or sewing silver coated fabric into knitted fabric;
   - normal yarn sections;
   - a power modification means to make the supplied power suitable for use;
   - an electronic controlling device to control positions and strength of the therapy; and
   - a plurality of separated heating pads configured to directly receive power from the conductive textiles to generate heat, the heating pads are made with a second conductive textile material having a second resistance that is higher than the first resistance,
   - 2N electrodes being in the middle of the heating pads which are made with a third conductive fabric having a third resistance lower than the second resistance, wherein the plurality of separated heating pads are connected with the power supply in parallel via the conductive textiles, and
   - wherein said heating pads and electrodes are strategically sized and positioned to provide the acupuncture therapy to the user.

2. The smart textile in claim 1, wherein a textile can take the form of underwear, sportswear, sweaters, knitwear, trousers, pants, briefs, brassieres, footwear, wrist/finger band support, ankle/foot band support, localized elbow and knee support bands, belts, bags, bed clothes, home products, or medical products.

3. The smart textile in claim 1, wherein input for power supply includes DC sources, AC sources, computer interfaces, or renewable energy sources.

* * * * *